United States Patent [19]

Bradshaw et al.

[11] Patent Number: 4,960,882

[45] Date of Patent: Oct. 2, 1990

[54] PROTON IONIZABLE MACROCYCLIC COMPOUNDS

[75] Inventors: Jerald S. Bradshaw; Reed M. Izatt; Virginia B. Christensen, all of Provo, Utah

[73] Assignee: Brigham Young University, Provo, Utah

[21] Appl. No.: 283,610

[22] Filed: Dec. 12, 1988

Related U.S. Application Data

[62] Division of Ser. No. 36,664, Apr. 8, 1987, abandoned.

[51] Int. Cl.$^5$ .................... C07F 9/655; C07D 498/06
[52] U.S. Cl. .................... 540/468; 540/469; 558/86; 556/404; 556/405
[58] Field of Search .................... 540/468, 469; 558/86; 556/404, 405

[56] References Cited

PUBLICATIONS

Bradshaw et al. "J. Heterocyclic Chem.", vol. 23, pp. 353–360, 361–368, 1667–1671, 1673–1676 (1986).

*Primary Examiner*—Robert T. Bond

[57] ABSTRACT

The invention relates to a composition of matter comprising compounds selected from the class consisting of

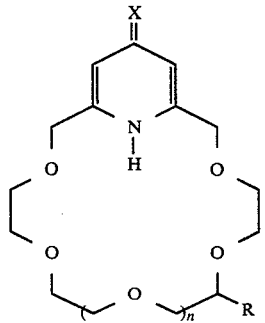

-continued
where X = O and S;
n = integers from -1 to 3, inclusive;
R = $C_{6-18}H_{13-37}$

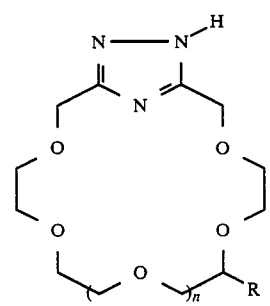

where n = integers from -1 to 3, inclusive;
R = $C_{6-18}H_{13-37}$

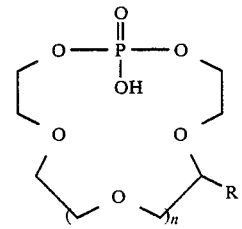

where n = integers from 1 to 4, inclusive;
R = $C_{6-18}H_{13-37}$ and (Abstract continued on next page.)

4,960,882
Page 2

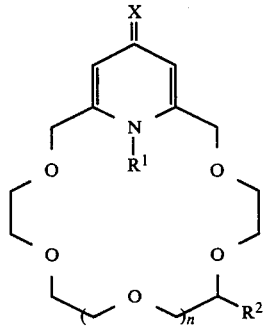

where X = O and S;
n = integers from
−1 to 3, inclusive;
$R^1$ = H and Blocker;
$R^2$ = $CH_2OCH_2CH=CH_2$,
$CH_2O(CH_2)_3Si(R^3)_2Cl$,
$CH_2O(CH_2)_3Si(R^4)_2O-$
SILICA GEL;
$R^3$ = $CH_3$ and Cl;
$R^4$ = $CH_3$ and O—
SILICA GEL

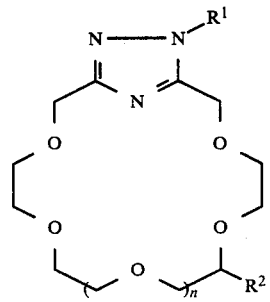

where X = O and S;
n = integers from
−1 to 3, inclusive;
$R^1$ = H and Blocker;
$R^2$ = $CH_2OCH_2CH=CH_2$,
$CH_2O(CH_2)_3Si(R^3)_2Cl$,
$CH_2O(CH_2)_3Si(R^4)_2O-$ -continued
SILICA GEL;
$R^3$ = $CH_3$ and Cl;
$R^4$ = $CH_3$ and O—
SILICA GEL

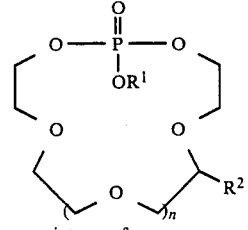

n = integers from
1–4, inclusive;
$R^1$ = H and Blocker;
$R^2$ = $CH_2OCH_2CH=CH_2$,
$CH_2O(CH_2)_3Si(R^3)_2Cl$,
$CH_2O(CH_2)_3Si(R^4)_2O-$
SILICA GEL;
$R^3$ = $CH_3$ and Cl;
$R^4$ = $CH_3$ and O—
SILICA GEL This process can be carried out in these ways: (A) as ligands in a liquid membrane phase for selectively; and competitively separating desired metal ions from mixtures with other ions in a separate source phase and transporting these ions to a separate receiving phase, with both of which the liquid membrane phase is in interfacial contact long enough to effect substantial removal of the desired ions from the source phase and transporting them to the receiving phase from which they are recovered, (B) as covalently bonded to silica gel supported in a column through which the multiple ion solution is first flowed, followed by receiving liquid, and (C) as ligand in an organic liquid filling pores or apertures in the wall of a hollow fiber in a bundle of hollow fibers on opposite sides of which flow the multiple ion solution and the receiving liquid.

16 Claims, 4 Drawing Sheets

PROTON IONIZABLE MACROCYCLIC COMPOUNDS

This application is a divisional application of our copending application Ser. No. 07/036,664, filed Apr. 8, 1987 and now abandoned.

INTRODUCTION

The present invention comprises a composition of matter which comprises certain proton-ionizable macrocyclic compounds which are particularly useful in separating a selected ion from a plurality of other ions in a multiple ion solution by bringing the multiple ion solution into contact with a compound of the invention in a number of different embodiments, each embodiment being capable of carrying out the unifying principle involving separating a desired ion from a multiple ion solution, e.g., a mixture thereof with other ions under selective, competitive conditions. Three specific embodiments of the process include bringing the multiple ion solution into contact with a compound of the invention (A) as a ligand in a liquid membrane for selective, competitive transport of desired metal ions complexed with said ligand from a separate source phase containing the mixture of ions to a separate receiving phase, where the separation means may be only the liquid membrane, as in an emulsion, or both a physical barrier and the liquid membrane as in an apparatus having a receiving vessel with an open-ended tube located in it with the liquid membrane phase immersing the lower end of the tube which contains one of the other phases and is surrounded by the other phase, (B) as an addition compound to silica gel in a separation column through which the mixture is first flowed to complex the desired ion with said compound followed by the flow through the column of a receiving liquid to break the complex, dissolve the desired ions and carry them out of the column, and (C) as a ligand in a liquid phase located in pores or apertures in the wall of each hollow filament in a bundle of filaments through which one of the other two phases flows while the other phase flows over the outsides of them. In each embodiment, the desired transported metal ions are recovered from the receiving phase by well known procedures.

More particularly, embodiment (A) of the process utilizing the compounds of the invention comprises the selective, competitive transport of desired metal ions from a source phase containing a mixture thereof with other ions by establishing a separate source phase containing the mixture of ions to be separated, a separate receiving phase, and a liquid membrane phase containing at least one such compound, e.g., a macrocyclic inner cavity proton-ionizable pyridone ligand, in a liquid membrane solvent phase interfacing with said source and receiving phases, maintaining the interfacial contact for a period of time long enough to transport a substantial part of the desired metal ions from the source phase to the receiving phase. This embodiment of the process may be referred to as selective transport of metal ions from a separate source phase to a separate receiving phase by a proton-metal ion coupled mechanism through a liquid membrane phase using macrocyclic ligands of the invention which have an ionizable proton. Embodiment (B) of the process utilizing compounds of the invention comprises forming a chemical covalent bond between a silica gel and at least one of the compounds, placing the resulting bonded silica gel in a tall column, causing the mixture of ions to flow through the column where the desired ions complex with the bonded silica gel which separates them from the rest of the mixture which flows out of the column, then flowing a receiving liquid through the column to break the complex, dissolve and carry out of the column the desired ions. Embodiment (C) of the process using compounds of the invention involves filling the apertures in the wall of each filament of a bundle of hollow filaments with a liquid containing the macrocyclic compound of the invention, flowing one of the two other phases through the filaments and the other phase over them while the macrocyclic compounds in the apertures transport the desired ions from the source phase to the receiving phase. In each embodiment the desired metal ions are recovered from the receiving phase by well known procedures.

BACKGROUND OF THE INVENTION

The fact is known that cyclic proton-ionizable pyridone polyethers, other cyclic polyethers and macrocyclic ligands are characterized by their size-related selectivity in binding cations, as noted by J. D. Lamb, R. M. Izatt, J. J. Christensen, D. J. Eatough, in *COORDINATION CHEMISTRY OF MACROCYCLIC COMPOUNDS*, edited by G. A. Melson, PLENUM, pages 145-217 (1979). A few macrocyclic compounds having a replaceable proton on a side chain have been disclosed for selective competitive alkali metal interactions such as in an article entitled *HIGH LITHIUM SELECTIVITY IN COMPETITIVE ALKALI-METAL SOLVENT EXTRACTION BY LIPOPHILIC CROWN CARBOXYLIC ACIDS* by Richard A. Bartch, Bronislaw P. Czech, Sang Ihn Kang, Louis E. Stewart, Wladyslaw Walkowiak, Witold A. Charewicz, Gwi Suk Heo and Byungki Son, J. Am. Chem. Soc., 1985, 107, 4997-4998. However, no proton-ionizable macrocycles of the type disclosed in the invention have been previously reported. Articles such as those entitled *ION-CHROMATOGRAPHIC SEPARATION OF SILICA GRAFTED WITH BENZO-18-CROWN-6 CROWN ETHER* by M. Lauth and Ph. Germain, J. Liquid Chromatogr., 1985, 8, 2403-2415, and *ION CHROMATOGRAPHY ON POLY(CROWN ETHER-MODIFIED) SILICA POSSESSING HIGH AFFINITY FOR SODIUM* by M. Nakajima, K. Kumura, E. Hayata, and T. Shono, J. Liquid Chromatogr., 1984, 7, 2115-2125, have disclosed the bonding of crown ethers to silica gels but they and all other known bonded silicas contain a benzene group or other electron withdrawing groups which reduce the ability of the macrocycle to bond with cations and other solutes and also involve secondary reactions of the silica gel with solutes, e.g., the interaction of the OH sites with metal cations. Prior researchers in this field confined their research to chromatographic applications and disclosed no concept of industrial separation applications where high purity products are required. No prior disclosure has been found of the attachment of proton-ionizable crown compounds to silica gel.

SUMMARY OF THE INVENTION

The compounds of the present invention are characterized by a replaceable or ionizable proton forming part of a macrocyclic compound having a lipophilic group attached to the molecule. It has been discovered that these compounds are particularly useful (A) as ligands in a liquid membrane for selectively transporting desired metal ions from a source phase to a receiving phase, (B) as addition compounds to silica gel chains for selectively complexing with desired metal ions as a source phase flows over them through a column followed by a receiving phase which breaks the complex and washes the desired metal ions out of the column, and (C) as transport agents in apertures in the wall of each filament in a bundle of filaments through which one of the two phases flows while the other flows over the outsides of them. These compounds are very effective and selective (1) as transporters or carriers of desired metal cations and (2) as complexing receivers of said metal cations. They are characterized in embodiment (A) of the invention by a high degree of transport selectivity for desired metal cations (according to the pH of both source and receiving phases and macrocyclic cavity size) over various other metal cations, a low solubility in water, which minimizes macrocycle loss to adjacent aqueous phases, and the formation of neutral cation complexes through the loss of a proton so that the anion does not need to accompany the cation through the membrane. This latter property makes it possible to couple the transport of cations to the reverse flux of protons through the membrane. They are characterized in embodiment (B) of the invention utilizing the compounds of the invention as addition compounds to silica gel chains in a column by high selectivity for and removal of desired metal ions from the source phase containing a mixture of metal ions as it flows over them in a column. They are characterized in embodiment (C) of the invention by a high degree of selectivity for removing the desired metal ions from the source phase and rapid transport of them through the short length of the ligand solution in the apertures of the walls of the filaments into the receiving phase. In all embodiments, the recovery of the desired metal ions from the receiving phase is easily accomplished by well known procedures.

BRIEF DESCRIPTION OF THE DRAWINGS

The invention will be described and illustrated by reference to the drawings in which.

DESCRIPTION OF PREFERRED EMBODIMENTS OF THE INVENTION

Preparation of the Compounds

The compounds of the invention may be prepared by any suitable method.

One method of preparing the compound of FIG. 3, for example, is to react the octyl-substituted triethylene glycol ditosylate and 4-(tetrahydro-2-pyranoxy)-2,6-pyridinedimethanol followed by acid hydrolysis as follows:

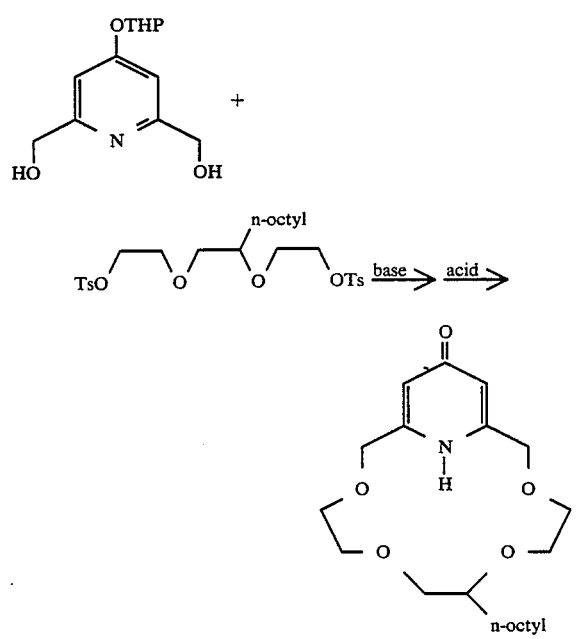

A method for producing the compound of FIG. 2 comprises reacting the ditosylate derivative of 4-THP blocked pyridinedimethanol and octyl substituted tetraethylene glycol as follows:

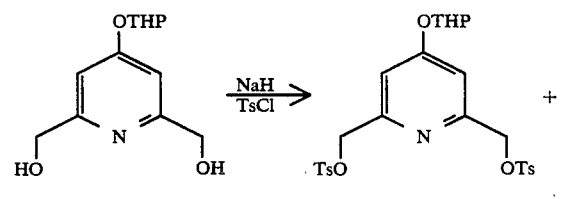

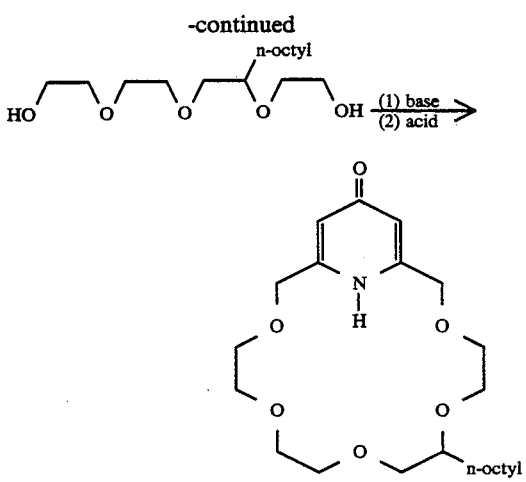

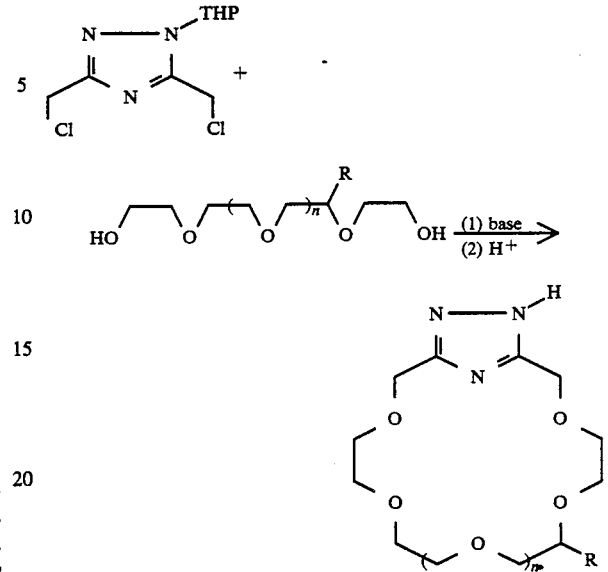

The synthesis of 4-pyridone compounds of the invention, which is not part of the present invention, is described in greater detail in an article entitled PROTON-IONIZABLE CROWN ETHERS. 3. SYNTHESIS AND STRUCTURAL STUDIES OF MACROCYCLIC POLYETHER LIGANDS CONTAINING A 4-PYRIDONE SUBCYCLIC UNIT by Jerald S. Bradshaw, Yohji Nakatsuji, Peter Huszthy, Bruce E. Wilson, N. Kent Dalley and Reed M. Izatt, J. Heterocyclic Chem., Vol. 23, pages 353-360 (1986), which is incorporated herein by reference.

The synthesis of the thiopyridone crown compounds of the invention (FIG. 4 in which X is sulphur) comprises treating the pyridone crowns in which X is oxygen with a good thionation reagent, e.g., $P_2S_5$ and 2,4-bis(4-methoxyphenyl)-1,3-dithia-2,4-diphosphetane-2,4-disulfide (Lawesson's Reagent, see Aldrich reagent number 22, 743-9).

The synthesis of the hydrogen phosphate containing compounds of the invention shown in FIG. 5 comprises reacting the appropriate oligoethylene glycol with phosphorus oxychloride followed by treating the crude chloride with water in dioxane as follows:

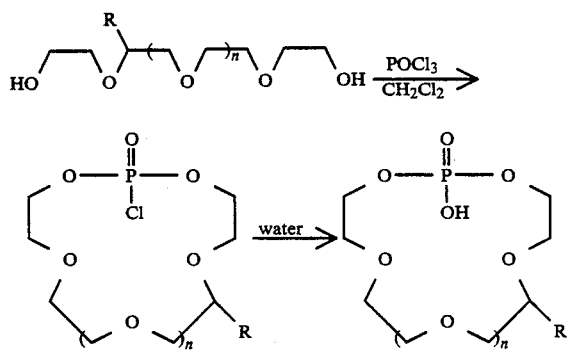

in which n is an integer from 0 to 3, inclusive, and R is $C_{6-18}H_{13-37}$.

Figure 13:
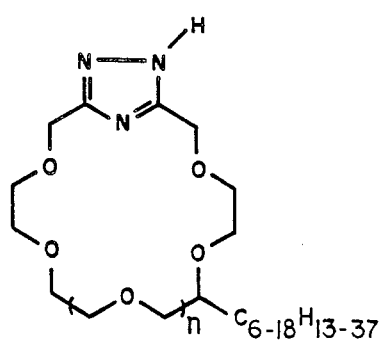
FIG. 13 represents another family of proton-ionizable compounds of the invention having a triazolo subcyclic ring system as part of the macrocycle.

The synthesis of the triazolo compounds shown in FIG. 13 comprises reacting the appropriate oligoethylene glycol with 1-N-THP-blocked-triazole-3,5-dimethylchloride followed by (1) base and (2) dilute acid to remove the blocking group as follows:

in which THP represents the tetrahydropyranyl block group, n=an integer from 0 to 3, inclusive, and $R=C_{6-18}H_{13-37}$.

Figure 7:
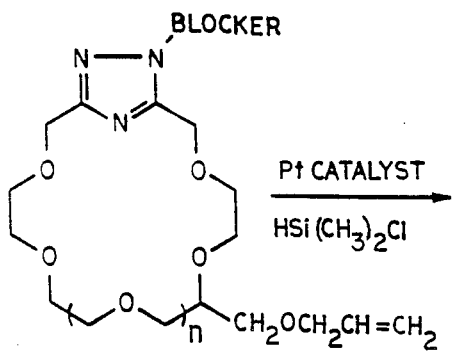
FIGS. 7, 8 and 9 represent the reactions involved in bonding a proton ionizable macrocycle to silica gel.
Figure 8:
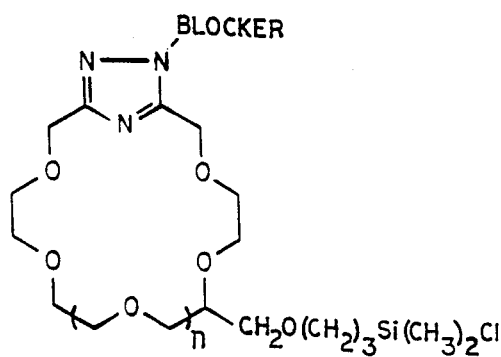
Figure 9:
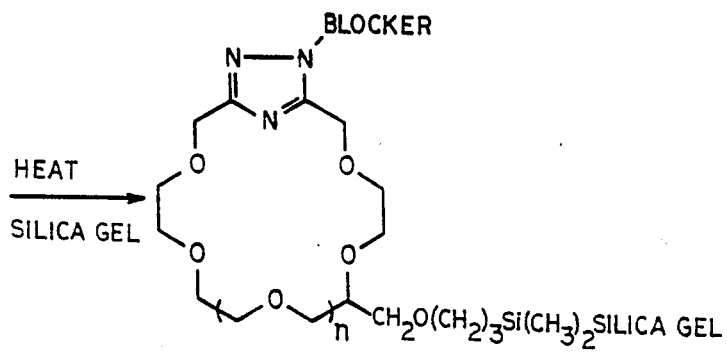

The formation of a crown compound covalently bonded to silica gel is illustrated in FIGS. 7, 8 and 9 of the drawing which comprises reacting a crown compound having a side chain —$CH_2$—O—$CH_2$—CH=$CH_2$ with HSi$(CH_3)_2$—Cl in the presence of a platinum catalyst to convert the side chain into —$CH_2$—O—$(CH_2)_3$—Si$(CH_3)_2$—Cl and heating this compound with silica gel to produce a crown compound linked to a silica gel by a side chain —$CH_2$—O—$(CH_2)_3$—Si$(CH_3)_2$—O—silica gel. The silicon atom in FIGS. 7 and 8 can have three attached chlorine atoms rather than two methyl groups and one chlorine. The compounds of FIGS. 4 and 5, and other species within the scope of FIG. 13, in addition to the one species illustrated in FIG. 7, can be used to form covalently bonded silica gel-crown compounds.

Metal Ion Recovery Process

The metal ion recovery process utilizing compounds of the invention relates to the selective recovery of desired metalions from mixtures thereof with other metal ions using the compounds of the invention as defined above. Effective methods of recovery and/or separation of metal ions, particularly lithium, sodium and potassium, from one another in waste solutions, deposits and industrial solutions and silver recovery from waste solutions, e.g., from emulsions on photographic and X-ray film, represent a real need in modern technology. The present invention accomplishes this separation effectively and efficiently by the use of compounds in the families represented by FIGS. 4 and 5, and more particularly by the compounds represented by FIGS. 2, 3, 7 and 13.

EMBODIMENT A

Figure 1:
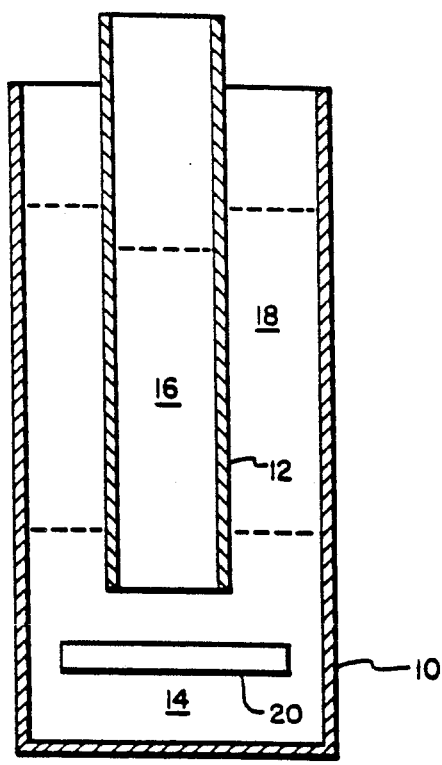
FIG. 1 is a diagramatic representation in vertical section of one form of apparatus which is suitable for use in embodiment (A) of the process of the invention.

Separation by use of a ligand-containing liquid membrane involves the transport of metal ions from a separate source phase to a separate receiving phase through the liquid membrane which interfaces with the two separate phases, e.g., as an emulsion or in an apparatus such as illustrated in FIG. 1 of the drawing which is described in detail hereinafter.

Figure 2:
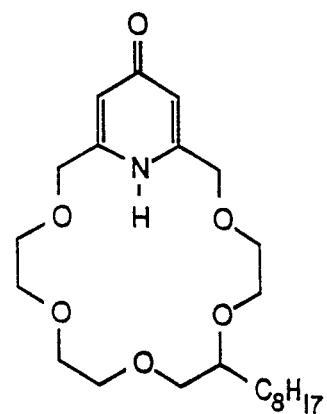
FIGS. 2 and 3 represent the molecular structures of two specific compounds of the invention, viz., octyl-substituted 4-pyridono-18-crown-6 and octyl-substituted 4-pyridono-15-crown-5, respectively, which are preferred embodiments of macrocylic compounds used in the process.

The cyclic compound of FIG. 2 exhibits the property of selectively complexing with $K^+$ under basic conditions at a source phase of pH=12 and higher and a receiving aqueous phase, e.g., $H_2O$, at pH=7 and $HNO_3$ at pH=1.5. The greater transport occurred with acid at pH=1.5 than with water at pH=7 as the receiving phase.

Figure 3:
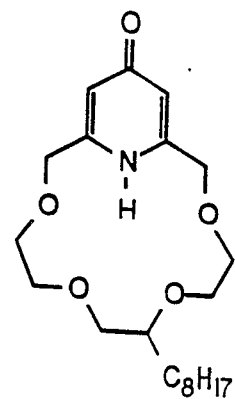

The cyclic compound of FIG. 3 exhibits the property of selectively complexing with $Li^+$ under basic conditions at a source phase of pH of 12 and higher and a receiving aqueous phase of water at pH=7 or $HNO_3$ at pH=1.5. Better transport of $Li^+$ was noted with a receiving phase of $H_2O$ at pH=7. This result apparently is due in part to the complexation of $Li^+$ by $OH^-$ to form LiOH(aq) in the receiving phase. The other alkali metal ions do not form similar MOH(aq) complexes.

A suitable apparatus in which the embodiment (A) of the process can be carried out is shown in FIG. 1 in which 10 represents an outer container having an open top and a bottom wall closing the bottom, 12 is an open-ended inner container of smaller cross sectional area than the cross sectional area of 10 located within container 10 with its open bottom end spaced above the bottom wall of the outer container, 14 is a layer of liquid membrane containing the ligand which is deep enough to cover the open bottom end of the inner container 12, 16 is the source phase, viz., a body of aqueous solution of the metal ions to be separated located in the inner container 12 above the liquid membrane, and 18 is an aqueous receiving phase located in the outer container 10 outside the container 12 above the level of the liquid membrane. A stirring means, e.g., a magnetic stirrer 20, may be included, if desired. In this apparatus the source phase 16 is separated from the receiving phase 18 by the liquid membrane 14 and by a physical barrier, the inner container 12, and the membrane phase. The containers may be made of any suitable material such as metal, glass, plastic and the like.

Embodiment (A) of the process is not dependent upon the use of this apparatus, however, because the process can be carried out in any apparatus which provides means for holding (1) a separate aqueous phase containing the metal ions to be separated, (2) a separate aqueous receiving phase and (3) a membrane phase which separates and interfaces with the other two phases. For example, the phases may be in any kind of container as an emulsion of the two separate aqueous phases as dispersed droplets in a continuous organic liquid phase containing the ligand. In such apparatus the source phase is separated from the receiving phase only by the liquid membrane phase.

In embodiment (A) of the process, the desired metal ions are selectively removed from the source phase 16 of the aqueous solution containing them by the deprotonated ligand in phase 14 across the interface between 14 and 16 and are delivered from the ligand to the aqueous receiving phase 18 across the interface between phases 16 and 18. The deprotonated hydrogen from the ligand forms water with the hydroxide from the source phase in the liquid membrane phase, causing the liquid membrane phase to become cloudy. Hydrogen from the receiving phase then protonates the ligand, being driven back across interfaces 16 and 18 through the liquid membrane phase, where the process repeats itself, causing a secondary driving force.

The separate aqueous phase containing the metal ions to be separated may be prepared in any suitable manner from any starting material having metal values which it is desired to recover in whole or in part.

The membrane phase containing the ligand in a suitable hydrophobic organic solvent may be prepared in any suitable manner from liquids known in the art to be useful for this purpose, e.g., any of those mentioned in J. D. Lamb, J. J. Christensen, J. L. Oscarson, B. L. Nielsen, B. W. Asay and R. M. Izatt, J. Am. Chem. Soc., 102, pages 6820-6824 (1980) which is incorporated herein by reference.

The receiving phase may be distilled water, deionized water, nitric acid solution in water having a suitable pH, e.g., 1-7, and the like.

The three liquid phases, after preparation, are placed in the apparatus in which the process is to be carried out.

In the apparatus without a physical barrier separating the source and receiving phases, the source phase and the receiving phase are emulsifed as separate droplets in a continuous liquid membrane phase in any suitable container.

In using the apparatus of FIG. 1, the membrane phase is first introduced into the container 10 until it covers the lower end of tube 12, as illustrated in FIG. 1, the receiving phase is introduced into the container 10 outside the tube 12, and the source phase is introduced into the tube 12 both floating on the membrane phase and separated by the tube 12. The transport of the metal ions from the source phase to the receiving phase then takes place through the membrane phase by means of the selective ligand over a long enough period of time for substantially complete removal of the desired metal ions from the source phase and their delivery to the receiving phase.

Working Examples of Embodiment A

Three liquid membranes are prepared of each of the two ligands represented by FIGS. 2 and 3, referred to sometimes hereafter as the compounds in FIGS. 2 and 3, respectively, by dissolving enough of each ligand in an organic liquid membrane solvent of methylene chloride to form a 1.0 mM solution.

Using the apparatus illustrated in FIG.1, into each of these 4-dram vials serving as outer containers 10 is poured 3.0 ml of each solution, which is enough to cover the lower end of inner glass tube 12. Atop this organic liquid are placed (1), in the space in container 10 outside the tube 12, 5.0 ml of distilled, deionized water, and (2) in the tube 12, 0.8 ml of a source phase containing the ions to be separated. After 24 hours the receiving phase is sampled by extracting 3 ml and analyzed for cation concentration by atomic absorption spectrometry. Three runs are made of each ligand and the results averaged. The standard deviation among the values in each run is less than 15%. The results are given in TABLES I, II, III and IV.

Table I gives the non-competitive fluxes of alkali metal ions from an aqueous source phase of various pH values across a liquid membrane phase containing the compound in FIG. 2 into either of two different receiving phases, either water at pH 7 or nitric acid at pH 1.5.

Table II gives the competitive fluxes of alkali metal ions from an aqueous source phase at pH 14 across a liquid membrane phase containing the compound of FIG. 2 into either of two different receiving phases. For each cation mixture the ratio of metal ion fluxes is also given.

Table III gives the non-competitive fluxes of alkali metal ions from aqueous source phases of various pH values across a liquid membrane phase containing the compound of FIG. 3 into receiving phases of either water at pH 7 or nitric acid at pH 1.5.

Table IV gives the competitive fluxes of alkali metal ions from an aqueous source phase at pH 14 across a liquid membrane phase containing the compound of FIG. 3 into either of two different receiving phases. For each cation mixture the ratio of metal ion fluxes is also given.

Fluxes are equal to $J_M$(moles/s-m$^2$)×10$^{-8}$ in which $J_M$ is the flux, s is seconds and m is meters.

TABLE I

Single M$^+$ fluxes$^a$ in a bulk H$_2$O-CH$_2$Cl$_2$-H$_2$O liquid membrane$^b$ system (FIG. 1) using the Compound of FIG. 2 as carrier.

| M$^+$ | Receiving Phase pH | Source Phase pH | | | | |
|---|---|---|---|---|---|---|
| | | 11 | 12 | 13 | 13.5 | 14 |
| Li$^+$ | 7 | — | — | — | — | 72 |
| | 1.5 | — | — | — | — | 56 |
| Na$^+$ | 7 | 6 | 9 | 47 | — | 503 |
| | 1.5 | 6 | 8 | 60 | — | 633 |
| K$^+$ | 7 | 6 | 32 | 375 | 920 | 805 |
| | 1.5 | 3 | 21 | 325 | 871 | 1631 |
| Rb$^+$ | 7 | <1 | 4 | 298 | 892 | 2032 |
| | 1.5 | 0 | 1 | 187 | 880 | 1601 |
| Cs$^+$ | 7 | 1 | 2 | 48 | 326 | 566 |
| | 1.5 | <1 | <1 | 55 | 327 | 779 |

$^a J_M$=(mol.s$^{-1}$.m$^{-2}$)10$^8$
$^b$Phase compositions: Source: 1.0 M in each metal cation using appropriate amounts of MNO$_3$ and MOH to achieve the initial source phase pH. Membrane: 1 mM of the Compound of FIG. 2 in CH$_2$Cl$_2$. Receiving: initial pH of 7 (H$_2$O) or 1.5 (HNO$_3$), as indicated.

TABLE II

Competitive M$^+$ fluxes$^a$ in a bulk H$_2$O—CH$_2$Cl$_2$—H$_2$O liquid membrane$^b$ system (FIG. 1) using the Compound of FIG. 2 as carrier

| Metal Ions $\dfrac{M_1^+}{M_2^+}$ | Aqueous Receiving Phase | | | |
|---|---|---|---|---|
| | pH = 7 | | pH = 1.5 | |
| | Flux | Ratio | Flux | Ratio |
| $\dfrac{K}{Li}$ | $\dfrac{1217}{17}$ | 71.5 | $\dfrac{1263}{6}$ | 210.5 |
| $\dfrac{K}{Na}$ | $\dfrac{1229}{263}$ | 4.7 | $\dfrac{2469}{375}$ | 6.6 |
| $\dfrac{K}{Rb}$ | $\dfrac{909}{332}$ | 2.7 | $\dfrac{1458}{601}$ | 2.4 |
| $\dfrac{K}{Cs}$ | $\dfrac{1021}{163}$ | 6.3 | $\dfrac{1715}{225}$ | 7.6 |

$^a J_M$ = (mol · s$^{-1}$ · m$^{-2}$)10$^8$
$^b$Phase compositions. Source: initial pH of 14, 0.5 M in each metal hydroxide. Membrane: 1 mM of the Compound of FIG. 2 in CH$_2$Cl$_2$. Receiving: initial pH of 7 (H$_2$O) or 1.5 (HNO$_3$), as indicated.

TABLE III

Single M$^+$ fluxes$^a$ in a bulk H$_2$O-CH$_2$Cl$_2$-H$_2$O liquid membrane$^b$ system using the Compound of FIG. 3 as carrier.

| M$^+$ | Receiving Phase pH | Source Phase pH | | | | |
|---|---|---|---|---|---|---|
| | | 11 | 12 | 13 | 13.5 | 14 |
| Li$^+$ | 7 | 2 | 4 | 50 | 2313 | 4254 |
| | 1.5 | 0 | 0 | 32 | 785 | 929 |
| Na$^+$ | 7 | 3 | 5 | 16 | 74 | 309 |
| | 1.5 | <1 | <1 | 7 | 209 | 641 |
| K$^+$ | 7 | 2 | 4 | 28 | 113 | 421 |
| | 1.5 | <1 | <1 | 5 | 111 | 461 |
| Rb$^+$ | 7 | <1 | 3 | 24 | 86 | 124 |
| | 1.5 | <1 | <1 | 5 | 83 | 135 |
| Cs$^+$ | 7 | <1 | 2 | 20 | 47 | 133 |
| | 1.5 | <1 | <1 | 4 | 174 | 246 |

$^a J_M$=(mol.s$^{-1}$.m$^{-2}$)10$^8$
$^b$Phase compositions: Source: 1.0 M in each metal cation using appropriate amounts of MNO$_3$ and MOH to achieve the initial source phase pH. Membrane: 1 mM of the Compound of FIG. 3 in CH$_2$Cl$_2$. Receiving: initial pH of 7 (H$_2$O) or 1.5 (HNO$_3$), as indicated.

TABLE IV

Competitive M$^+$ fluxes$^a$ in a bulk H$_2$O—CH$_2$Cl$_2$—H$_2$O liquid membrane$^b$ system FIG. 1) using the Compound of FIG. 3 as carrier.

| Metal Ions $\dfrac{M_1^+}{M_2^+}$ | Aqueous Receiving Phase | | | |
|---|---|---|---|---|
| | pH = 7 | | pH = 1.5 | |
| | Flux | Ratio | Flux | Ratio |
| $\dfrac{Li}{Na}$ | $\dfrac{449}{228}$ | 2.0 | $\dfrac{1443}{630}$ | 2.3 |
| $\dfrac{Li}{K}$ | $\dfrac{474}{184}$ | 2.6 | $\dfrac{1074}{237}$ | 4.5 |
| $\dfrac{Li}{Rb}$ | $\dfrac{753}{353}$ | 2.1 | $\dfrac{545}{232}$ | 2.4 |
| $\dfrac{Li}{Cs}$ | $\dfrac{507}{172}$ | 2.9 | $\dfrac{892}{317}$ | 2.8 |
| $\dfrac{Na}{K}$ | $\dfrac{193}{181}$ | 1.1 | $\dfrac{519}{245}$ | 2.1 |
| $\dfrac{Na}{Rb}$ | $\dfrac{612}{767}$ | 0.8 | $\dfrac{339}{79}$ | 4.3 |
| $\dfrac{Na}{Cs}$ | $\dfrac{857}{833}$ | 1.0 | $\dfrac{302}{147}$ | 2.1 |
| $\dfrac{K}{Rb}$ | $\dfrac{223}{335}$ | 0.7 | $\dfrac{310}{384}$ | 0.8 |
| $\dfrac{K}{Cs}$ | $\dfrac{138}{215}$ | 0.6 | $\dfrac{178}{219}$ | 0.8 |
| $\dfrac{Rb}{Cs}$ | $\dfrac{268}{242}$ | 1.1 | $\dfrac{237}{256}$ | 0.9 |

$^a J_M$ = (mol · s$^{-1}$ · m$^{-2}$)10$^8$.
$^b$Phase compositions. Source: initial pH of 14, 0.5 M in each metal hydroxide. Membrane: 1 mM of the Compound of FIG. 3 in CH$_2$Cl$_2$. Receiving initial pH of 7 (H$_2$O) or 1.5 (HNO$_3$), as indicated.

TABLE II demonstrates selective transport of K$^+$ over other alkali metal cations with the solution of the compound in FIG. 2 at high pH with both H$_2$O and HNO$_3$, pH=1.5 as receiving phases. TABLE IV demonstrates selectivity for Li$^+$ and, to a lesser degree, Na$^+$ over other alkali cations with the compound of FIG. 3 at high pH with both H$_2$O, pH=7, and HNO$_3$, pH=1.5 as receiving phases.

While the compounds of the invention do not depend for patentability on the reason or hypothesis for the difference in selectivity, it may be noted that the two ligands vary in the size of their central cavities. The alkali metal ions decrease in size as follows: Cs$^+$=1.70 A; Rb$^+$=1.48 A; K$^+$=1.36 A; Na$^+$=1.01 A; Li$^+$, 0.67 A. It may well be that the selectivity is a function of a complexing relation between cavity size and cation size.

The competitive flux data in TABLE II demonstrate that K$^+$ is transported selectively by the larger-cavity pyridone ligand of FIG. 2. Reducing the cavity size to that of the compound of FIG. 3 results in selective transport of Na+ and Li+ over the remaining cations, as seen in Table IV. In this latter case, Li+ is transported selectively over Na+ by 2.3 fold. A further improvement in Li+ selectively over Na+ is to be expected with a still smaller cavity pyridone macrocycle of FIG. 4 when n=0.

It is likely that M+ selectivity is related to the relative hydration energies of the cations studied, since partial or complete dehydration of the cation occurs in the complexation process.

Experiments were carried out using the compound of FIG. 2 to measure the rate of K+ transport under conditions of varying source phase pH values, which demonstrates the exchange of a proton for the cation at the source phase interface, but $H_2O$ (H+ from the ligand and OH− from the source phase) may be pulled into the liquid membrane phase. This is evidenced by the degree of cloudiness (which coincides with the degree of transport) in the liquid membrane phase.

Figure 6:
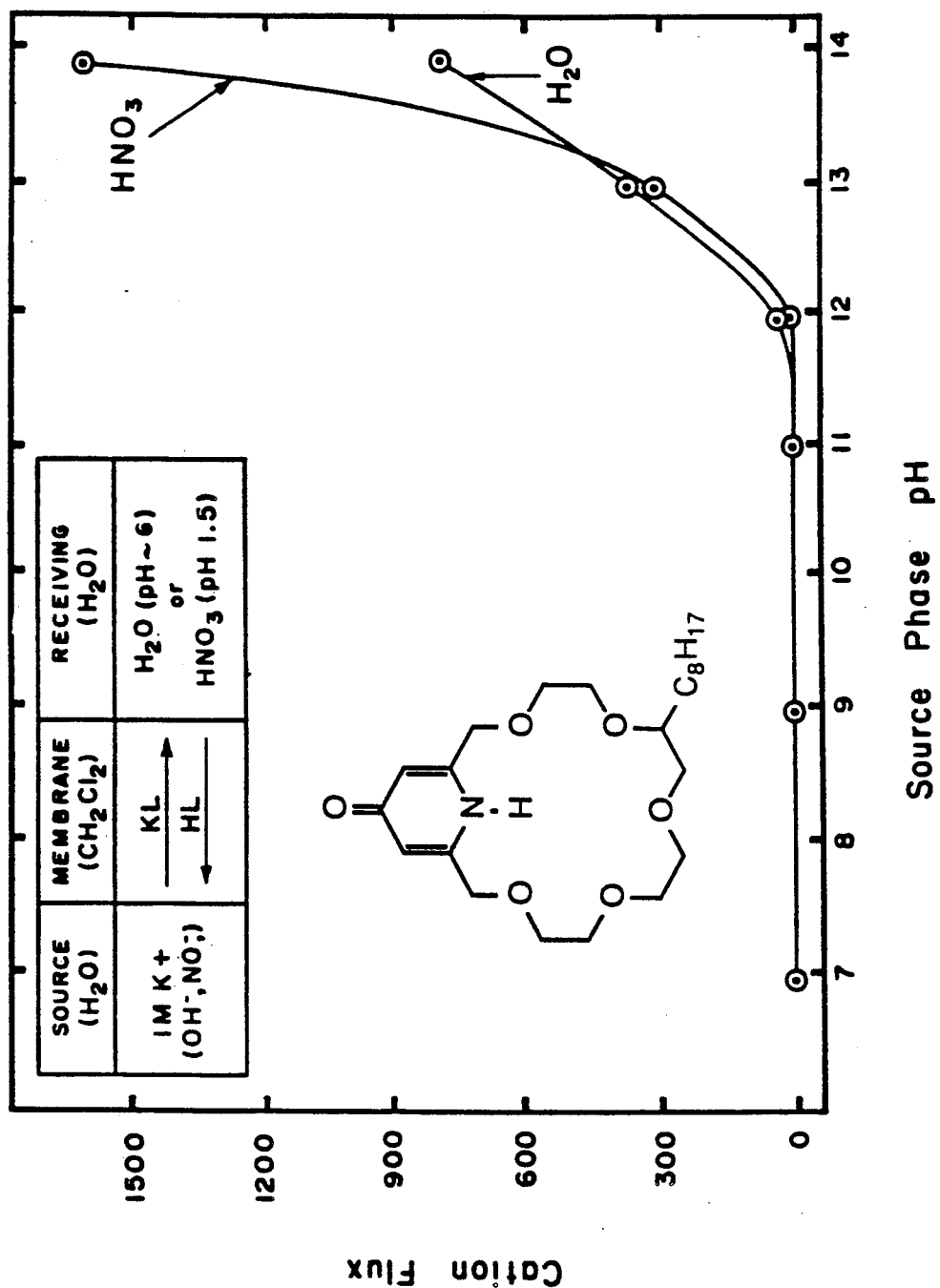
FIG. 6 represents the plot of cation flux from a source phase at pH values from 7 to 14 into a receiving phase of water at pH 6 or nitric acid at pH 1.5 using the compound shown in FIG. 2 as the ligand in the membrane phase.

Mixtures of MNO$_3$ and MOH were used as the source phase. The relative amounts of the two solutes were adjusted to maintain the total M+ concentration at 1.00M in each case. The transport rates are small below pH 12 but rise rapidly at pH values above 12, as seen in FIG. 6. This result confirms the fact that a proton is removed from the ligand in the complexation process and that for appreciable transport to take place, the source phase must be quite basic (pH>12).

Tests of transport of various metal ions at various beginning pH values of the receiving phase were carried out in the manner described previously using various macrocyclic compounds of the invention with results compiled in Tables V through IX as follows:

Table V, Transport of lithium metal ions by the compound of FIG. 3.

Figure 4:
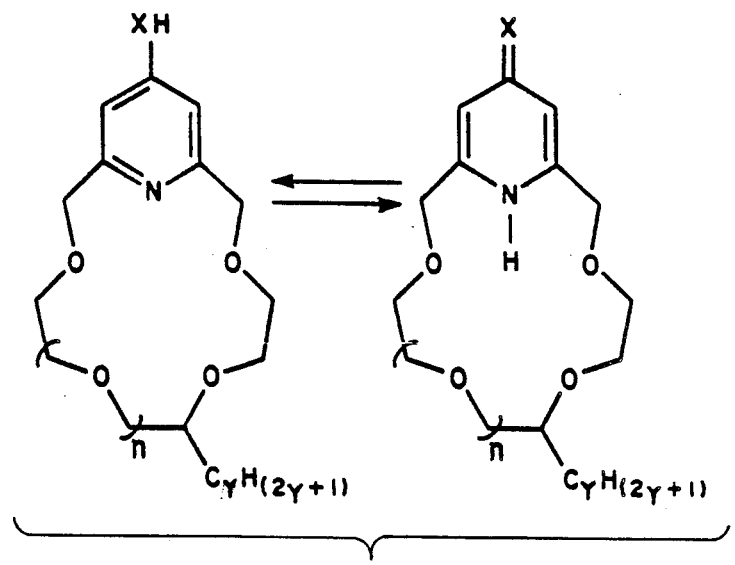
FIG. 4 represents two isomers a and b of one family of proton-ionizable macrocyclic compounds of the invention in which n is an integer from 0 through 4, inclusive, X is chosen from the group consisting of oxygen and sulfur and y is an integer from 6 through 18, inclusive. In solution, the 4-hydroxypyridine structure of FIG. 4a is in equilibrium with the pyridone structure of FIG. 4b.

Table VI, Transport of silver metal ions by the compound of FIG. 4 in which x=0 and n=1.

Table VII, Non-competitive fluxes of alkali metal ions by the sulfur analog (X=S, n=2, y=8) of the compound of FIG. 4 from an aqueous source phase at various pH values across a liquid membrane phase into two different receiving phases, either water at pH 7 or nitric acid at pH 1.5.

Table VIII, Competitive fluxes of alkali metal ions from an aqueous source phase at pH 14 across the liquid membrane phase containing the compound of FIG. 4 (X=S, n=2, y=8) into a nitric acid receiving phase. Column a gives the mixture of ions in the source phase. Column b gives the ratio of alkali metal fluxes in a receiving phase of nitric acid of pH 1.5.

Figure 5:
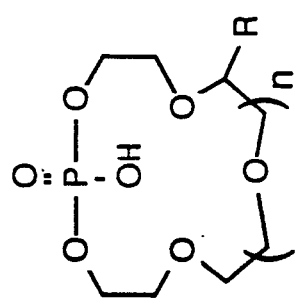
FIG. 5 represents another family of proton-ionizable compounds of the invention having a hydrogen phosphate group in the macrocyclic molecule.

Table IX, Non-competitive fluxes of alkali metal ions from an aqueous source phase of various pH values across a liquid membrane phase containing the compound of FIG. 5 into two different receiving phases, either water at pH 7 or nitric acid at pH 1.5.

TABLE X gives data on separations of silver from lead effected in apparatus of the type illustrated in FIG. 1 using proton-ionizable triazolo crown ethers.

TABLE V

Fluxes of Lithium Metal Ions in Liquid Membrane Systems[c](FIG. 1) using the Compound of FIG. 3

| [a]Beginning pH | 7.00 | 4.20 | 3.13 | 2.03 | 1.44 |
|---|---|---|---|---|---|
| [a]Ending pH | >12.33 | >12.27 | >12.38 | 11.97 | 1.58 |
| [b]Fluxes | 4254 | 3798 | 4785 | 3224 | 929 |

[a]Receiving phase pH and source phase pH(lithium hydroxide) = >13.3
[b]Fluxes = $(mol.s^{-1}.m^{-2}) \times 10^8$
[c]Membrane system = 1 mM of the Compound of FIG. 3 in $CH_2Cl_2$

TABLE VI

Fluxes of Silver Metal Ions in Liquid Membrane Systems[c](FIG. 1) using the Compound of FIG. 4*

| [a]Beginning pH | 6.80 | 4.08 | 3.13 | 2.03 | 1.42 |
|---|---|---|---|---|---|
| [a]Ending pH | 4.49 | 3.93 | 3.05 | 2.05 | 1.41 |
| [b]Fluxes | 607 | 520 | 663 | 451 | 289 |

[a]Receiving phase pH and source phase pH(silver nitrate) = 6.9
[b]Fluxes = $(mol.s^{-1}.m^{-2}) \times 10^8$
[c]Membrane system = 1 mM of the Compound of FIG. 4* in $CH_2Cl_2$
*X = 0, Y = 8 and n = 1.

TABLE VII

Single M+ fluxes[a] in a bulk $H_2O$—$CH_2Cl_2$—$H_2O$ liquid membrane[b] system(FIG. 1) using the Compound of FIG. 4* as carrier.

| M+ | Receiving Phase pH | Source Phase pH | | | | |
|---|---|---|---|---|---|---|
| | | 11 | 12 | 13 | 13.5 | 14 |
| Li+ | 7 | 22 | 51 | 56 | 84 | 266 |
| | 1.5 | 1 | 12 | 18 | 39 | 153 |
| Na+ | 7 | 84 | 116 | 118 | 124 | 54 |
| | 1.5 | 26 | 46 | 151 | 563 | 172 |
| K+ | 7 | 844 | 604 | 713 | 568 | 122 |
| | 1.5 | 168 | 473 | 712 | 935 | 733 |
| Rb+ | 7 | 299 | 366 | 363 | 298 | 66 |
| | 1.5 | 44 | 158 | 420 | 578 | 328 |
| Cs+ | 7 | 136 | 173 | 222 | 133 | 67 |
| | 1.5 | 43 | 61 | 211 | 239 | 243 |

[a]$J_M=(mol.s^{-1}.m^{-2})10^8$
[b]Phase compositions: Source: 1.0 M in each metal cation using appropriate amounts of MNO$_3$ and MOH to achieve the initial source phase pH. Membrane: 1 mM of the Compound of FIG. 4* in $CH_2Cl_2$. Receiving: initial pH of 7 ($H_2O$) or 1.5 ($HNO_3$), as indicated.
*X = S, Y = 8 and n = 2.

TABLE VIII

Competitive M+ fluxes[a] in a bulk $H_2O$—$CH_2Cl_2$—$H_2O$ liquid membrane[b] system (FIG. 1) using the Compound of FIG. 4a* as carrier.

| a | b | a | b | a | b |
|---|---|---|---|---|---|
| $\frac{Li}{K}$ | $\frac{\leq 1}{225}$ | $\frac{Li}{Rb}$ | $\frac{1}{277}$ | $\frac{Li}{Cs}$ | $\frac{10}{275}$ |
| $\frac{K}{Rb}$ | $\frac{248}{84}$ | $\frac{K}{Cs}$ | $\frac{231}{27}$ | $\frac{Rb}{Cs}$ | $\frac{196}{46}$ |

[a]= system
[b]= ratio of metal ion fluxes, receiving phase pH = 1.5 and source phase pH = 14
*X = S, Y = 8, n = 2.

TABLE IX

Single M+ fluxes[a] in a bulk $H_2O$—$CH_2Cl_2$—$H_2O$ liquid membrane[b] system(FIG. 1) using the Compound of FIG. 5 as carrier.

| M+ | Receiving Phase pH | Source Phase pH | | | | |
|---|---|---|---|---|---|---|
| | | 11 | 12 | 13 | 13.5 | 14 |
| Li+ | 7 | 7 | 11 | 11 | 18 | 29 |
| | 1.5 | 7 | 27 | 35 | 34 | 26 |
| Na+ | 7 | 43 | 76 | 49 | 53 | 43 |
| | 1.5 | 87 | 218 | 246 | 305 | 191 |
| K+ | 7 | 37 | 49 | 52 | 55 | 52 |
| | 1.5 | 94 | 187 | 621 | 745 | 1099 |
| Rb+ | 7 | 39 | 57 | 70 | 54 | 53 |
| | 1.5 | 55 | 202 | 338 | 851 | 661 |
| Cs+ | 7 | 36 | 51 | 50 | 84 | 36 |

TABLE IX-continued

Single $M^+$ fluxes[a] in a bulk $H_2O-CH_2Cl_2-H_2O$ liquid membrane[b] system(FIG. 1) using the Compound of FIG. 5 as carrier.

| $M^+$ | Receiving Phase pH | Source Phase pH | | | | |
|---|---|---|---|---|---|---|
| | | 11 | 12 | 13 | 13.5 | 14 |
| | 1.5 | 80 | 191 | 169 | 238 | 621 |

[a]$J_M = (mol.s^{-1}.m^{-2})10^8$
[b]Phase compositions: Source: 1.0 M in each metal cation using appropriate amounts of $MNO_3$ and MOH to achieve the initial source phase pH. Membrane: 1 mM of the Compound of FIG. 5 in $CH_2Cl_2$. Receiving: initial pH of 7 ($H_2O$) or 1.5 ($HNO_3$), as indicated.

TABLE X

Single $Ag^+$ and $Pb^{2+}$ and Competitive $Ag^+$ vs $Pb^{2+}$

| Crown Ether[a] | Receiving Phase pH[b] | Flux[c]$((mol.s^{-1}.m^{-2})10^8)$ | | | |
|---|---|---|---|---|---|
| | | $Ag^+$ (single) | $Pb^{2+}$ (single) | $Ag^+$ vs | $Pb^{2+}$ |
| Octyl-triazolo-15C5 | 7 | 55 | 293 | 56 | 1 |
| | 1.5 | | | 452 | 2 |
| Octyl-triazolo-18C6 | 7 | 328 | 876 | 420 | 87 |
| | 1.5 | 1019 | 61 | 1303 | 73 |
| Dicyclohexano-triazolo-18C6 | 7 | 276 | 401 | 720 | 7 |
| | 1.5 | 1927 | 246 | 1549 | 8 |
| Dibenzotri-azolo-18C6 | 7 | 30 | 2 | 47 | <1 |
| | 1.5 | 253 | <1 | 288 | <1 |

[a]1 mM of compound analogs in $CH_2Cl_2$
[b]pH 7 = $H_2O$; pH 1.5 = $HNO_3$
[c]The source phase was 1.0 M in each of the cations present An analog of the compound in FIG. 3 (described above as highly selective for lithium at source phase pH=14) is the compound in FIG. 4a (X=0, n=1, y=8) which shows a high transport for silver at source phase pH=6.9 and at receiving phase pH=1.5 ($HNO_3$). Transport more than doubled with the receiving phase at pH=7 ($H_2O$) as seen in Table VI.

In the transport of silver ions the compound in FIG. 4a (X=0, n=1, y=8) shows the proton shifted to the oxygen atom on top, with the pyridone ring bonding structure modified to the 4-hydroxy pyridine structure so that an anion must accompany the metal across the system. Lower transport of $Ag^+$ with acid receiving phase is due to the anion $NO_3^-$ in the receiving phase inhibiting transport of $Ag^+ + NO_3^-$ across the interface.

Silver transport by the compound in FIG. 4a (X=0, n=1, y=8) in an emulsion liquid membrane parallels transport in the bulk liquid membrane. An emulsion liquid membrane is similar to a bulk liquid membrane, except that the membrane separates the aqueous source phase and receiving phase by surrounding the receiving phase as an emulsified droplet. In the emulsions studied, the source phase contained 0.001M $AgNO_3$, the membrane was a 0.02M macrocycle solution in toluene, sorbitan monooleate was used as the surfactant (3% v/v) and the receiving phase contained either $MgS_2O_3$ (0.1M) or $HNO_3$ (pH=1.5). After 30 minutes, 98% of the $Ag^+$ was transported when $MgS_2O_3$ was present in the receiving phase compared to 12% transport when $HNO_3$ was present in the receiving phase. The difference in the amounts of transport is due to a transport mechanism where $NO_3^-$ is co-transported across the membrane by the macrocycle as seen in the bulk liquid membrane experiments.

The sulfur analog of the compound in FIG. 4 (see FIG. 4b: X=S, n=2, y=8) appears to have a decrease in transport at source phase pH=14 (Table VII) but is still selective for $K^+$ over other alkali metals in competitive systems (Table VIII). This sulfur analog allows selective transport at lower pH source phase ranges.

Phosphorous proton-ionizable compounds have also shown high transport rates (Table IX) with results similar to those shown in Table VII.

TABLE X gives data on separations of silver from lead effected in apparatus of the type illustrated in FIG. 1 using proton-ionizable triazolo crown ethers. In all cases, silver is transported selectively over $Pb^{2+}$. Using a pH 7 or lower source phase, all other cations tested (alkali and alkaline earth cations, $Fe^{3+}$, $Ca^{2+}$, $Ni^{2+}$, and $Zn^{2+}$) showed little or no transport. Greater transport of $Ag^+$ with an acidic receiving phase indicates that the transport of $Ag^+$ by these triazolo macrocycles proceeds by a proton-ionizable mechanism.

An emulsion liquid membrane consisting of 0.9 ml of 0.03M bis(octyl)triazolo-18-crown-6 in phenylhexane as the membrane, 9 ml of 0.001M $AgNO_3$ and 0.001M $PbNO_3)_2$ as the source phase and 0.9 ml of an $HNO_3$ receiving phase (pH=1.5) transferred 70% of the $Ag^+$ and only 1% of the $Pb^{2+}$ initially present in the source phase in 30 minutes.

A solvent extraction system of 4 ml of 0.03M bis(octyl)triazolo-18-crown-6 in phenylhexane and 4 ml of 0.001M $AgNO_3$ in water extracted $Ag^+$ into the phenylhexane phase quantitatively by a proton-ionizable mechanism. Triazolo-type macrocycles are selective for $Ag^+$ over all other cations tested.

EMBODIMENT B

Figure 10:
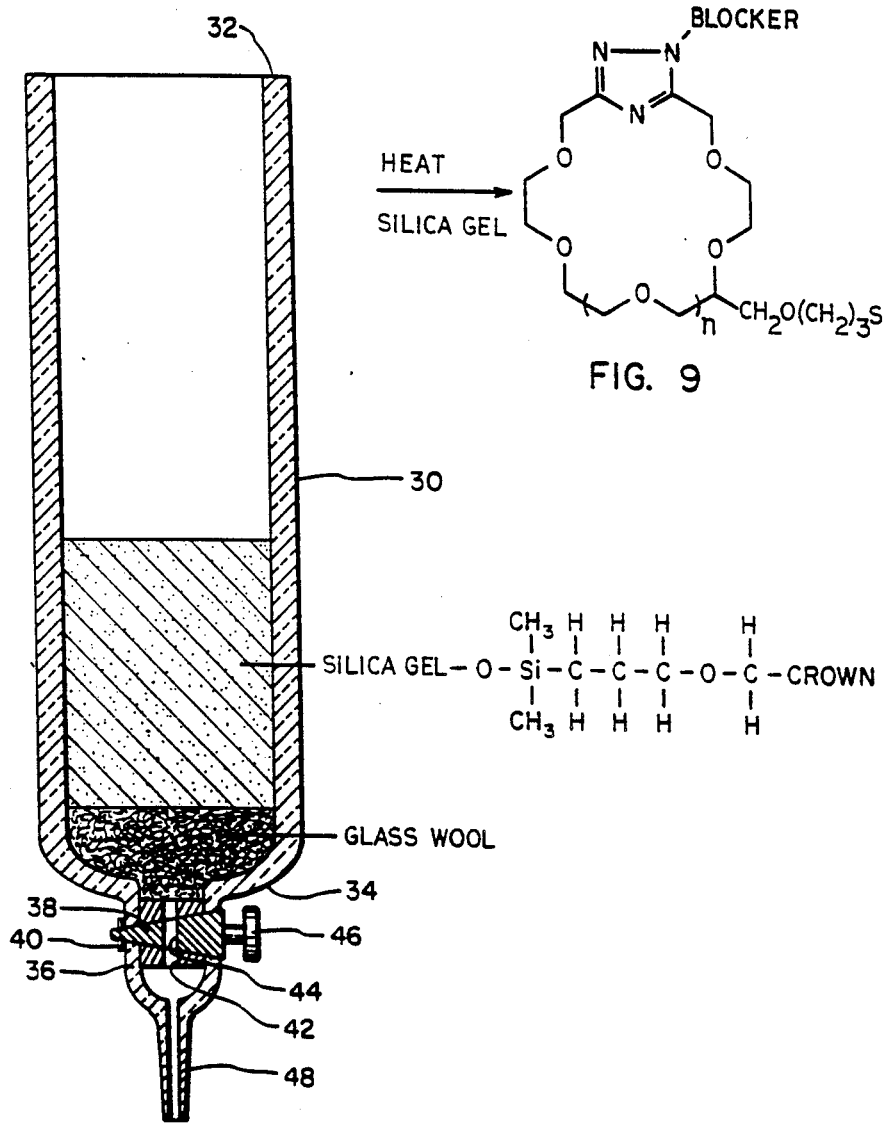
FIG. 10 represents schematically a suitable column for holding the silica gel-proton ionizable addition compound through which a solution of metal ions can be flowed to complex selectively with a desired ion in accordance with embodiment (B) of the process.

In this embodiment of the process, a column is packed over a support of glass wool with a macrocycle covalently bonded to silica gel as illustrated in FIG. 10 in which the column is designated generally by reference number 30 and comprises a wall 32 of any suitable material, e.g., glass, tapering at the bottom 34 to a closure member comprising a plug 36 having a petcock 38 rotatable therein by means of a handle 46. Plug 36 has a liquid passage 42 capable of communicating with the column and the atmosphere when the petcock is open. Petcock 38 has a passageway through it which in one position aligns with passage 42 to permit discharge of liquid from the column through a nozzle 48 into any suitable container (not shown) and in other positions prevents such discharge. A support layer of glass wool is placed in column 30 above the outlet 42, as shown, which adequately supports a layer of the silica gel-crown compound complex placed above it without interfering with the flow of liquid through the gel-crown layer.

A suitable method of preparing the complex of silica gel with a crown compound is illustrated in FIGS. 7, 8 and 9. The crown compound of FIG. 7 in which n may be 0–3 is reacted in the presence of a platinum catalyst with $HSi(CH_3)_2Cl$ to yield the compound of FIG. 8 which is then reacted by heat with silica gel to yield the crown-bonded silica gel of FIG. 9. A sufficient quantity thereof is then placed in the column 30 on top of the glass wool support to yield a layer deep enough to complex the crown compound with substantially all of the desired cation contained in the multi-cation liquid flowed through the column.

The selective complexing properties of these compounds are retained while the stability of packed silica gel columns is maintained. Furthermore, these separations correlate directly to the equilibrium constants for solute-macrocycle interaction in solution, as shown in the following working examples.

The process of Embodiment B can be carried out with other crown compounds from the other families disclosed by using a compound selected from these classes in the process represented by FIGS. 7, 8 and 9, respectively, instead of the compound shown in each of these Figs.

Working Examples of Embodiment B

A silica gel-containing crown-ether pendant groups was synthesized by passing a mixture of 1.0 gram of dimethylchlorosilane (freshly distilled) and 2.1 grams of benzene through an activated charcoal column having a diameter of 1 centimeter and a length of 45 centimeters to remove any trace impurities. 2.0 grams of the crown alkene were heated to 85° C. in a 25 milliliter round bottom flask fitted with a reflux condenser and purged with argon gas for an hour. The catalyst $H_2PtCl_6$ was added as 15 microliter of a 0.4% solution (98 THF, 1 EtOH, 1 $H_2PtCl_6$). The reaction proceeded for 10 hours. This mixture was then added to 25.0 grams of silica gel (60–200 mesh, dried at 350° C. for 4 hours and at 250° C. for 6 hours) suspended in $CCl_4$. The mixture was stirred and heated at reflux for an additional 24 hours. The silica gel was then collected by filtration and washed 5 times with $CH_2Cl_2$ (25 ml portions) and three times with MeOH (25 ml portions). The final product was dried and the washings were checked to determine the yield. Based on the residue, the yield for the process was 99%.

One column containing unbonded silica gel was prepared to examine whether any separations observed were due to interactions of solutes with silica gel rather than the macrocycle. A second column was prepared by packing it with silica gel bonded to 18-crown-6. The height and diameter of both cylindrical columns were 150 centimeters and 19 centimeters, respectively. The exact same procedure was followed with each column. All tests were done in triplicate and the standard deviation in the tests was always less than 5% of the mean.

In each test a solute-containing water solution was passed through the columns until the concentrations leaving the columns were equivalent to the concentrations entering them so that the columns would be at equilibrium with the solute-containing solution. The columns were then washed with sufficient water to remove any solutes from the column which were not bound to the column. The use of 200 ml of water was found to be sufficient for the solute concentrations used. An eluent solution was then flowed through the columns until no solutes could be detected in the solution emerging from the columns. The following solute-containing water solutions were used: (A) $Sr(NO_3)_2$ (Fisher) vs. $Mg(NO_3)_2$ with both nitrates present at 0.1, 0.01 and 0.001M; (B) $Sr(NO_3)_2$ vs. $Ca(NO_3)_2$ (Baker & Adamson) with both nitrates present at 0.1 and 0.001M; (C) 0.5M $Ca(NO_3)_2$ vs. 0.001M $Sr(NO_3)_2$; (D) 0.1M $Sr(NO_3)_2$ vs. either 0.1M, or 0.001M $Ba(NO_3)_2$ (Baker); and (E) 0.9M $Mg(NO_3)_2$ vs. 0.1M $Ca(NO_3)_2$ vs. 0.001M $Sr(NO_3)_2$.

The alkaline earth cations used interact with 18-crown-6 in water and are easily eluted from the column with acetate or citrate. A 1.0M citrate buffer prepared from 1.0M citric acid (Fisher) and 2.5M LiOH (Pierce) was used as the eluent solution except when $Ba^{2+}$ was one of the cations present. Since the solubility of barium citrate is low, a 1.0M acetic acid (J. T. Baker) and 0.5M LiOH buffer was used as the eluent when $Ba^{2+}$ was present. Citrate is the preferred eluent because the equilibrium constants for citrate-alkaline earth cation interactions are greater than the corresponding constants for acetate. Since the equilibrium constants for the interactions of both citrate and acetate with various alkaline earth cations are similar, the eluent will have little effect on the separations performed. All solutions collected from the columns were analyzed for the appropriate alkaline earth cation concentrations by atomic absorption spectrophotometry (Perkin Elmer Model 603).

Results of Working Examples of Embodiment B

Bonded silica has OH sites which may also interact with alkaline earth cations and since this interaction, if it occurs, would affect the separation selectivity, the selectivity of pure silica gel for alkaline earth cations is given in TABLE XI in the column headed "Blank Column Selectivity." An alternative method for determining the selectivity of the macrocycle may be used where the interaction properties of the two cations with the OH groups are the same but one cation preferentially interacts with the macrocycle. This is done by placing the less interactive cation in excess of the other cation so that nearly all of the OH sites will interact only with the less macrocycle-interactive cation and any change in selectivity observed will then be due to the interactive properties of the macrocycle. In TABLE XI the selectivity of 18-crown-6-covalently-bonded-silica gel for alkaline earth cations is given. An example of using the data in TABLE XI to determine macrocycle selectivity for one cation over another is provided by the $Ba^{2+}/Sr^{2+}$ system. When $Sr^{2+}$ is present in excess of $Ba^{2+}$ (bottom two entries) the $Ba^{2+}/Sr^{2+}$ selectivity is increased approximately ten-fold in comparing the data for the Blank and Macrocycle columns. This ten-fold selectivity is consistent with the equilibrium constants for macrocycle-cation interaction reported in the literature.

TABLE XI

| Separation of Alkaline Earth Cations using an 18-crown-6 Bonded Silica Gel | | | |
|---|---|---|---|
| Selectivity Ratio | Cation Concentrations | Macrocycle Column Selectivity | Blank Column Selectivity |
| $Sr^{2+}/Mg^{2+}$ | 0.1 M $Sr^{2+}$ 0.1 M $Mg^{2+}$ | 17.0 17.0 | 1.34 |
| $Sr^{2+}/Mg^{2+}$ | 0.01 M $Sr^{2+}$ 0.01 M $Mg^{2+}$ | 23.5 | 0.88 |
| $Sr^{2+}/Mg^{2+}$ | 0.001 M $Sr^{2+}$ 0.001 M $Mg^{2+}$ | 23.6 | 1.14 |
| $Sr^{2+}/Ca^{2+}$ | 0.1 M $Sr^{2+}$ 0.1 M $Ca^{2+}$ | 3.3 | 0.99 |
| $Sr^{2+}/Ca^{2+}$ | 0.01 M $Sr^{2+}$ 0.01 M $Ca^{2+}$ | 2.6 | 0.74 |
| $Sr^{2+}/Ca^{2+}$ | 0.001 M $Sr^{2+}$ 0.5 M $Ca^{2+}$ | 0.154 | 0.0025 |
| $Sr^{2+}/Mg^{2+}$ | 0.001 M $Sr^{2+}$ | 0.54 | 0.00813 |
| $Sr^{2+}/Ca^{2+}$ | 0.1 M $Ca^{2+}$ | 0.54 | 0.00685 |
| $Sr^{2+}/Mg^{2+}$ | 0.9 M $Mg^{2+}$ | 1.0 | 1.2 |
| $Ba^{2+}/Sr^{2+}$ | 0.1 M $Ba^{2+}$ 0.1 M $Sr^{2+}$ | 2.8 | 1.3 |
| $Ba^{2+}/Sr^{2+}$ | 0.01 M $Ba^{2+}$ 0.1 M $Sr^{2+}$ | 0.5 | 0.056 |
| $Ba^{2+}/Sr^{2+}$ | 0.001 M $Ba^{2+}$ 0.1 M $Sr^{2+}$ | 0.105 | 0.011 |

EMBODIMENT C

Figure 11:
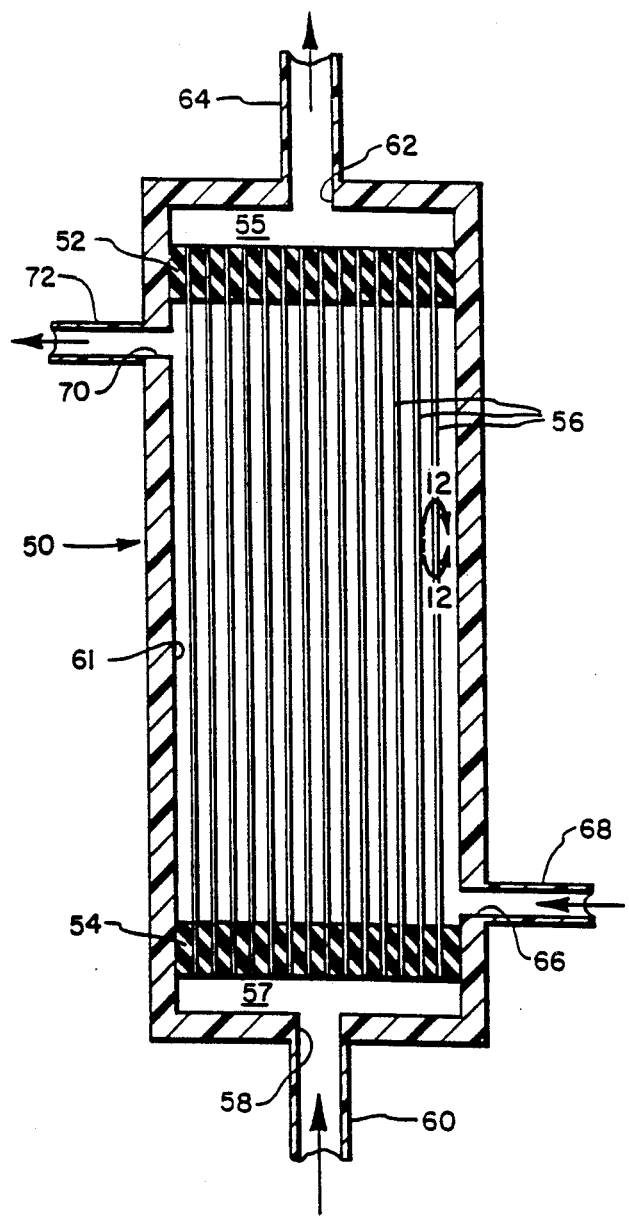
FIG. 11 represents a suitable apparatus for carrying out embodiment (C) of the process.
Figure 12:
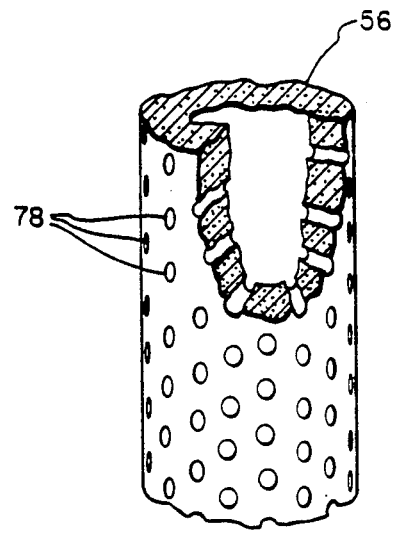
FIG. 12 is a fragmentary perspective view of a short length of a filament on a much larger scale to show apertures in the wall thereof.

Referring now to FIGS. 11 and 12, reference number 50 designates a casing having an internal header 52 secured near one end so as to leave an open chamber 55 and a like internal header 54 secured near the other end so as to leave an open chamber 57. In and between headers 52 and 54 in a chamber 61 individual hollow fibres 56 are mounted as shown. Casing 50 has an inlet opening 58 into chamber 57 communicating with a supply line 60 for a multi-cation liquid. This liquid enters each filament and flows through it into chamber 55 at the other end of casing 50 from which it flows out through opening 62 into exhaust line 64. The chamber 61 in casing 50 between headers 52 and 54 in which the bundle of filaments 56 is located has an inlet opening 66 communicating with a liquid supply line 68 and an outlet opening 70 communicating with a line 72.

FIG. 12 shows the structure of a portion of an individual hollow fiber 56 in which the cylindrical wall is provided with a large number of tiny pores or apertures 78. Each aperture is filled with a ligand-containing organic solvent of the type described in Embodiment A by filling chamber 61 with its liquid phase, flowing the organic liquid-ligand phase through inlet 58 followed by the other liquid phase to be flowed through the apparatus which flushes out the organic liquid except from the pores or apertures 78. The very short distance between the two phases through the organic-ligand liquid which occupies the pores or apertures of the hollow fiber gives a very short path of transport for the cations by the ligand from the multi-cation liquid on one side of the wall of the hollow fiber to the receiving liquid on the other side of it.

In use, the liquid containing the cations to be separated is usually flowed through the hollow interior of the fibers 56 and receiving liquid through chamber 61 but this is not essential and may be reversed, if desired. In any event the flow of the multi-cation liquid and the receiving liquid on opposite sides of the wall of hollow fiber 56 gives good contact of the macrocyclic crown compounds situated in each aperture 78 with both liquids which are separated by the very short distance of the wall thickness of the hollow fibers, making the length of transport of the selected desired cation very short and the efficiency of the transport very high.

Examples from our work using hollow fiber liquid membranes containing a particular macrocycle to make separations include separating $K^+$ from other alkali cations and $Sr^{2+}$ from other alkaline earth cations. A phenylhexane solution containing a hydrophobic analog of dicyclohexano-18-crown-6 was used as the membrane. Specifically, when all cations were present in the source phase as $NO_3^-$ salts at 0.1M the macrocycle was present at 0.05M in the membrane and the receiving phase was water, $K^+$ was transported over $Na^+$ by a factor of 60 and $Sr^{2+}$ was transported over $Ba^{2+}$ by a factor of 2. The macrocycles described in the invention can be used similarly in a hollow fiber system.

Although the invention has been described and illustrated by reference to certain specific proton-ionizable compounds and processes of using them, analogs of these macrocycles are within the scope of the compounds and processes of the invention.

Having thus described and illustrated the invention, what is claimed is:

1. Compounds selected from the group consisting of

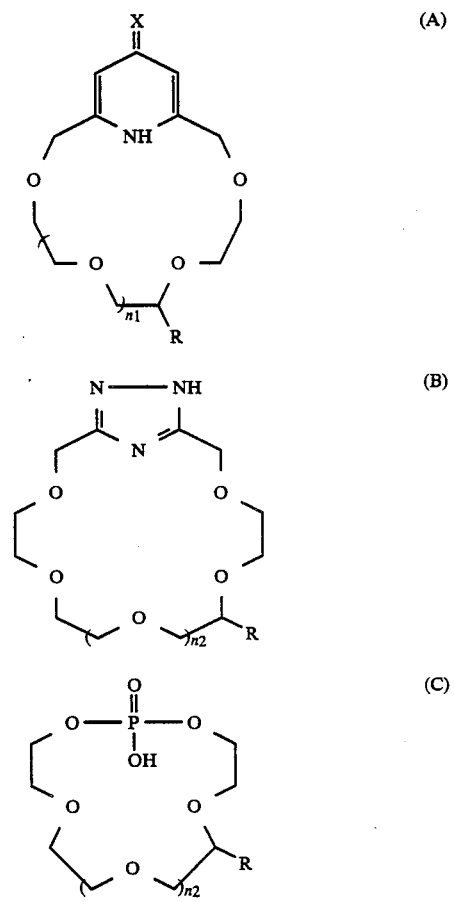

where X is a member selected from the group consisting of O and S; R is a hydrocarbon chain having from 6 to 18 carbon atoms and 13 to 37 hydrogen atoms; $n_1$ is an integer from 0 to 4; and $n_2$ is an integer from 0 to 3.

2. The compound A as set forth in claim 1 in which X is 0.

3. The compound A as set forth in claim 1 in which X is S.

4. The compound A as set forth in claim 1 in which $n_1$ is 0 and R is $C_8H_{17}$.

5. The compound A as set forth in claim 1 in which $n_1$ is 1, and R is $C_8H_{17}$.

6. The compound A as set forth in claim 1 in which $n_1$ is 2 and R is $C_8H_{17}$.

7. The compound A as set forth in claim 1 in which $n_1$ is 3 and R is $C_8H_{17}$.

8. The compound B as set forth in claim 1 in which $n_2$ is 0 and R is $C_8H_{17}$.

9. The compound B as set forth in claim 1 in which $n_2$ is 1 and R is $C_8H_{17}$.

10. The compound B as set forth in claim 1 in which $n_2$ is 2 and R is $C_8H_{17}$.

11. The compound B as set forth in claim 1 in which $n_2$ is 3 and R is $C_8H_{17}$.

12. The compound C as set forth in claim 1 in which $n_2$ is 0 and R is $C_8H_{17}$.

13. The compound C as set forth in claim 1 in which $n_2$ is 1 and R is $C_8H_{17}$.

14. The compound C as set forth in claim 1 in which $n_2$ is 2 and R is $C_8H_{17}$.

15. The compound C as set forth in claim 1 in which $n_2$ is 3 and R is $C_8H_{17}$.

16. Compounds selected from the group consisting of

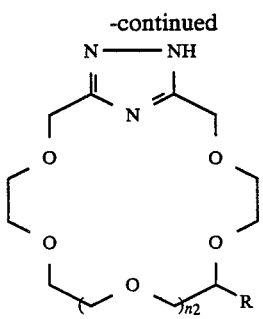
(A)

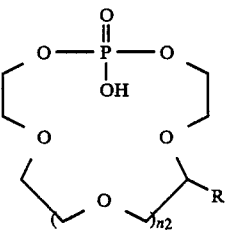
(B)

(C)

where X is a member selected from the group consisting of O and S; R is a member selected from the group consisting of $CH_2OCH_2CH=CH_2$, $CH_2O(CH_2)_3Si(R^2)_2Cl$, and $CH_2O(CH_2)_3Si(R^3)_2O$-Silica Gel; $R^2$ is selected from the group consisting of $CH_3$ and Cl; $R^3$ is selected from the group consisting of $CH_3$ and O-silica gel; $n_1$ is an integer from 0 to 4; and $n_2$ is an integer from 0 to 3.

* * * * *